United States Patent [19]

Garrido

[11] Patent Number: 5,194,253
[45] Date of Patent: Mar. 16, 1993

[54] AQUEOUS GEL, USABLE IN COSMETICS, BASED ON HYALURONIC ACID AND DEOXYRIBONUCLEIC ACID, AND A PREPARATION PROCESS

[75] Inventor: Ricardo Garrido, Chateauroux, France

[73] Assignee: Pier Auge (Societe Anonyme), Chateauroux, France

[21] Appl. No.: 477,914

[22] PCT Filed: Sep. 8, 1989

[86] PCT No.: PCT/FR89/00452
§ 371 Date: May 9, 1990
§ 102(e) Date: May 9, 1990

[87] PCT Pub. No.: WO90/02774
PCT Pub. Date: Mar. 22, 1990

[30] Foreign Application Priority Data

Sep. 9, 1988 [FR] France ................. 88 11787

[51] Int. Cl.$^5$ .............. A61K 7/02; A61K 7/48; A61K 37/10; A61K 31/725
[52] U.S. Cl. ................. 424/78.03; 424/401; 424/402; 424/484; 424/485; 424/487; 424/488; 514/772.6; 514/777; 514/781; 514/782; 514/844; 514/944; 523/105
[58] Field of Search ............ 424/78, 81, 484, 485, 424/487, 488, 78.31, 78.03; 514/844–848, 944; 523/105, 111

[56] References Cited

U.S. PATENT DOCUMENTS

| 4,178,361 | 12/1979 | Cohen et al. | 424/487 |
| 4,707,354 | 11/1987 | Garlen et al. | 424/47 |
| 4,965,071 | 10/1990 | Kawan | 424/78 |

Primary Examiner—T. K. Page
Assistant Examiner—E. J. Webman
Attorney, Agent, or Firm—Oblon, Spivak, McClelland, Maier & Neustadt

[57] ABSTRACT

An aqueous gel based on hyaluronic acid and on deoxyribonucleic acid usable in cosmetics, and a method of preparation.

The invention relates to an aqueous gel formed by a homogeneous mix of:
a) an alkaline salt or an ammonium salt of hyaluronic acid in the form of an aqueous gel;
b) a mineral or organic salt of high molecular weight deoxyribonucleic acid in the form of an aqueous gel;
c) at least one hydrophilic polymer having the property of forming aqueous film-forming gels.

Application to the preparation of masks in cosmetics.

3 Claims, No Drawings

AQUEOUS GEL, USABLE IN COSMETICS, BASED ON HYALURONIC ACID AND DEOXYRIBONUCLEIC ACID, AND A PREPARATION PROCESS

The invention relates to a novel aqueous gel based on hyaluronic acid and on highly polymerised deoxyribonucleic acid, a process for its preparation, and also its use in cosmetics for the preparation of a skin treatment mask.

Hyaluronic acid is a high molecular weight polysaccharide which forms an important component of the extracellular matrix of conjunctive tissues, in particular in the skin, the tendons, the cartilages and the muscles. Hyaluronic acid may for example be obtained in the form of its sodium salt by extraction from cockscomb, and its industrial production by bacterial fermentation is envisaged. It displays a very great capability for retention of water in the form of a solution or of a gel having pseudo-plastic properties and a visco-elastic flow.

Hyaluronic acid and its salts, in particular its sodium salt, are used in cosmetic products having a beneficial effect on the skin, in particular due to the fact that aqueous solutions of hyaluronic acid have an excellent hydrating effect.

Elsewhere, it has been proposed to use reticulated gels based on hyaluronic acid to hold a substance having a biological or pharmacological activity and to progressively liberate this substance, in a controlled manner, on contact with the skin. Such reticulated gels and their use are, for example, described in the patent FR-A-2,574,414.

The patent application JP-A-59.134706 describes a composition for hydration of the skin, containing nucleic acids, a hydrating agent such as hyaluronic acid, and various active constituents. A gel intended for the preparation of a cosmetic mask, comprising an alginate, a salt of a bivalent metal, a phosphate, an anionic surface-active agent and a filler such as $SiO_2$, $ZnO$, $Al_2O_3$, etc., is described in the patent application EP-A-0045493.

It is an object of the present invention to provide a homogeneous aqueous gel comprising on the one hand hyaluronic acid, and on the other hand another substance capable of effecting a beneficial action on the skin, in the form of an aqueous gel, this gel being in an appropriate form for its application to the skin, more particularly as a cosmetic treatment mask, and having the property of being able to be very rapidly hardened, at least on the surface, in such a way as to produce a coherent film by a process which is simple and easy to regulate, without giving off heat or liberating or bringing into play a toxic substance.

Accordingly, the aqueous gel according to the invention is characterised in that it is essentially formed of a homogeneous mix of a) an alkaline salt or an ammonium salt of hyaluronic acid in the form of an aqueous gel;

b) a mineral or organic salt of deoxyribonucleic acid of high molecular weight in the form of an aqueous gel;

c) at least one hydrophilic polymer having the property of forming aqueous film-forming gels.

The expression "having the property of forming aqueous film-forming gels" refers to a hydrophilic polymer capable of forming a non-reticulated gel or an aqueous solution having pseudo-plastic properties, it being possible for this gel or this solution to be easily and rapidly transformed into a coherent plastic film by any appropriate process, for example by insolubilisation or reticulation.

According to a preferred embodiment of the invention, it is advantageous to use as a hydrophilic polymer having the property of forming aqueous film-forming gels, an alginate of an alkali metal or an ammonium alginate, and preferably a sodium alginate. The sodium alginate also has the advantage of being haemostatic and of encouraging the healing of wounds or cuts in the skin, which improves the properties of the gel of the invention.

It is also preferable, according to the present invention, to use as a salt of hyaluronic acid, an alkaline salt such as sodium hyaluronate and, as a salt of deoxyribonucleic acid, a sodium salt, a calcium salt, a magnesium salt, a manganese salt, a lysine salt, or an arginine salt, and more particularly a sodium salt. It is important, according to the present invention, that the deoxyribonucleic acid, in the salt form, be highly polymerised.

The highly polymerised deoxyribonucleic acid, or high molecular weight deoxyribonucleic acid, is a commercially available product obtained from germinative cells of eukaryotic organisms, originating for example from fish roe, by an adapted extraction process comprising a deproteination operation on the starting material in a medium of raised ionic force, and also a fibrous flocculation operation in an alcoholic medium.

The product thus obtained, comsisting of a mineral salt or an organic salt, preferably a sodium salt, of deoxyribonucleic acid, exists in the dehydrated state in the form of fibres of white to creamy-white colour having a length of several centimetres.

This product is soluble in the water when forming aqueous solutions or aqueous gels which behave as a non-Newtonian liquid having pseudo-plastic flow. Such solutions are radically distinguishable from ordinary commercial aqueous solutions of deoxyribonucleic acid, of low molecular weight, such as for example the standard deoxyribonucleic acid according to the French Pharmacopoeia, whose flow is always of a Newtonian type.

The sodium salt of high molecular weight deoxyribonucleic acid, or of highly polymerised deoxyribonucleic acid, usable in the present invention, is for example the salt marketed by the Javenech Company (Fougeres, France).

According to a particularly advantageous form of the invention, the aqueous gel according to the present invention is formed by a homogeneous mix containing a) 0.1 to 1% by weight of an alkaline salt or of an ammonium salt of hyaluronic acid;

b) 1 to 3% by weight of a mineral salt or of an organic salt of deoxyribonucleic acid of high molecular weight;

c) 1 to 3% by weight of at least one hydrophilic polymer having the property of forming aqueous film-forming gels;

d) a sufficient quantity of water to make it up to 100%.

It is preferable that the gel according to the present invention also contain a preservative which may be chosen from any of the appropriate substances, acceptable in cosmetics, and for example dehydroacetic acid and its salts, sorbic acid, a paraben, a preservative known under any one of the commercial names Kathon CG, Sepicide HB, Germall II, Germaben II, Phenonip CLR, Nipastat, Bronopol, Methoxyde soda, Preserval and Paridol. These preservatives may be used alone or in combinations of two or several, as the case may be.

According to one embodiment of the present invention, the gel may contain a thickener, which thus allows reducing the quantity of hyaluronic acid salt used. This thickener is used preferably in a quantity less than or equal to 5% by weight with respect to the total weight of the gel. Any thickener commercially known and acceptable in cosmetics may be used in the invention on condition that it be compatible with the hydrophilic polymer and in particular with the sodium alginate, but there is preferably used a derivative of polyacrylic acid, a cellulosic derivative, carrageenans, a guar gum or a carob gum or an xanthan gum, and for example the product derived from polyacrylic acid marketed under the trade mark Carbopol (Goodrich). These thickeners may be used alone or in combination, and for example a carrageenan/carob combination, a xanthan/carob combination or a xanthan/guar combination may be used.

The aqueous gel according to the present invention may of course contain, apart from the principal constituents, the preservatives and the thickener indicated above, any appropriate supplementary ingredient, such as for example a substance having a biological or pharmacological action, a substance having as its function optimising the physical properties of the gel, in particular its rheological properties, or yet again its chemical or physico-chemical properties, for example its pH, a perfume, a colourant, etc.

The invention also extends to a method for the preparation of the aqueous gel described above, which is distinguished in that a gel having pseudo-plastic properties is prepared from an alkaline salt or from an ammonium salt of hyaluronic acid, to it is added at least one hydrophilic polymer having the property of forming film-forming aqueous gels, a gel is prepared from a mineral or organic salt of high molecular weight deoxyribonucleic acid in a non-Newtonian form, having pseudo-plastic properties, which is added to the said gel of hyaluronic acid salt, and the whole is mixed in such a manner as to obtain a homogeneous gel.

Preferably, the gel of hyaluronic acid salt is a gel prepared from a solution of 1% in water and the gel of deoxyribonucleic acid is a gel prepared from a solution of 5% in water even though these values may be modified depending on the required properties.

The aqueous gel based on hyaluronic acid and on deoxyribonucleic acid according to the present invention may be used in cosmetics to produce a cosmetic treatment mask by applying to the skin to be treated at least one layer of gel, by covering the said layer of gel with a gauze, then with a second layer of gel on the gauze, by effecting the transformation of the second layer of gel into a plastic film, by later removing the plastic film thus formed, the first non-transformed layer of gel then remaining on the skin.

In the case where the hydrophilic polymer having the property of forming aqueous film-forming gels is an alginate of an alkaline metal or an ammonium alginate, and in particular a sodium alginate, the transformation of the layer of gel, containing an alginate, into a film is preferably brought about by spraying an aqueous solution of an alkaline salt or an alkaline earth salt, acceptable in cosmetics, over the entire surface of the layer, and by then leaving this solution to act on the layer of gel for a time sufficient to totally transform the said layer of gel into a plastic film.

The salt in aqueous solution sprayed onto the surface of the gel to bring about the formation of the film is preferably calcium chloride.

The characteristics and advantages of the present invention will appear in more detail in the following example given by way of a non-limiting example.

EXAMPLE

An aqueous gel having the following composition is prepared from an aqueous solution of sodium hyaluronate, to which is added a sodium alginate, then an aqueous gel of 5% by weight of a sodium salt of high molecular weight deoxyribonucleic acid (ADN Integral Javenech), which is mixed (except where indicated otherwise, the percentages and ratios are indicated by weight):

| | |
|---|---|
| Sodium hyaluronate (aqueous gel of 1% by weight) | 77.8% |
| Gel of high molecular weight deoxyribonucleic acid (DNA) (aqueous gel of 5% by weight of the sodium salt of DNA) | 20.0% |
| Sodium Alginate (Protanal SF sold by the Protan A/S company, Norway) | 2.0% |
| Preserving agent (sorbic acid) | 0.2% |

This gel may be used for the application of a cosmetic treatment mask to the face and the neck.

Before application of the mask to the face, the skin is cleaned by means of a cleansing lotion or a cream comprising microbeads.

A first layer of gel is applied to the face and the neck, and a massage encouraging commencement of penetration of the active constituents contained in the gel into the first layers of the epidermis is carried out. A second layer of gel is then applied, then the face and the neck are covered with a gauze which must remain stuck to the gel over the entire surface to be treated. Finally, a thin second layer of gel is applied over the gauze.

A finely atomized aqueous solution of 10% by weight of calcium chloride, $CaCl_2$, is then carefully sprayed over the entire surface of the gel.

This solution is allowed to act for about 30 minutes, which brings about practically complete plastification of the superficial layer of the mask, to form a coherent plastic film. During this time, the active constituents contained in the first layer of gel in contact with the skin are absorbed by the layers of the epidermis.

The film is then removed, and the face is cleaned in the usual way.

This treatment allows restoring the hydrolipid balance of the skin due to the very pronounced hydrating effect of the gel.

In particular, the following beneficial effects on the skin are observed:
  powerful anti-wrinkle effect;
  improvement in the sebaceous secretion and regulation of the superficial hydro-lipid film;
  considerable increase in the elasticity and in the firmness of the teguments;
  the effect of an exceptional increase in the freshness of the complexion;
  very effective photo-protection power;
  favourable structural modifications, detectable by appropriate examination, of the dermo-epidermal constituents.

Trials carried out have shown that the gel according to the present invention described above is perfectly harmless.

I claim:

1. A method of forming a cosmetic treatment mask comprising:
   i) applying to skin to be treated at least one layer of an aqueous gel which comprises a homogenous mixture of:
      a) 0.1-1% by weight of an alkaline salt or an ammonium salt of hyaluronic acid;
      b) 1-3% by weight of a mineral or organic salt of deoxyribonucleic acid in the form of an aqueous gel, wherein said aqueous gel of a mineral or organic salt of deoxyribonucleic acid behaves as a non-Newtonian liquid having pseudo-plastic flow;
      c) 1-3% by weight of at least one hydrophilic polymer having the property of forming aqueous film-forming gels; and
      d) a sufficient quantity of water to make the percentage of ingredients up to 100%;
   ii) covering said layer of aqueous gel with gauze;
   iii) applying a second layer of said aqueous gel to said gauze;
   iv) transforming said second layer of aqueous gel into a plastic film; and
   v) removing said plastic film;
   wherein said layer according to step i) remains on the skin.

2. The method of claim 1, wherein said hydrophilic polymer having the property of forming aqueous film-forming gels is an alginate of an alkali metal or an ammonium alginate; and
   wherein said transformation step iv) is performed by spraying an aqueous solution of an alkali or alkaline-earth salt acceptable in cosmetics over the entire surface of said second layer and allowing said solution to act on said second layer for a time to sufficient to entirely transform said second layer into a plastic film.

3. The method of claim 2, wherein said alkaline-earth salt acceptable in cosmetics is calcium chloride.

* * * * *